(12) United States Patent  (10) Patent No.: US 6,431,025 B1
Koros et al.  (45) Date of Patent: Aug. 13, 2002

(54) RATCHET MECHANISM FOR A SURGICAL RETRACTOR ASSEMBLY

(76) Inventors: Tibor Koros; Gabriel Koros, both of 610 Flinn Ave., Moorpark, CA (US) 93021

( * ) Notice: Subject to any disclaimer, the term of this patent is extended or adjusted under 35 U.S.C. 154(b) by 0 days.

(21) Appl. No.: 09/143,558

(22) Filed: Aug. 31, 1998

Related U.S. Application Data

(63) Continuation-in-part of application No. 29/059,029, filed on Aug. 30, 1996, now Pat. No. Des. 397,791.

(51) Int. Cl.[7] .......................... G05G 1/00; A61B 17/02
(52) U.S. Cl. .................. 74/577 M; 74/535; 74/537; 74/540; 74/577 R; 600/228; 600/232; 600/234
(58) Field of Search ..................... 74/575, 577 R, 74/577 S, 577 M, 578, 535, 537, 538, 540; 600/227–235, 201

(56) References Cited

U.S. PATENT DOCUMENTS

| | | | | |
|---|---|---|---|---|
| 4,421,108 A | * | 12/1983 | Cabrera et al. | 600/234 |
| 4,424,724 A | * | 1/1984 | Bookwalter et al. | 74/540 |
| 5,375,481 A | * | 12/1994 | Cabrera et al. | 74/577 M |
| 5,755,660 A | * | 5/1998 | Tyagi | 600/232 |

* cited by examiner

Primary Examiner—David A. Bucci
Assistant Examiner—William C Joyce
(74) Attorney, Agent, or Firm—Richard D. Slehofer

(57) ABSTRACT

A ratchet mechanism for a surgical retractor blade having a dual ratchet holder. A pivot ratchet is mounted on the dual ratchet holder. A pawl key mounted on the dual ratchet holder. The pawl key is used to engage the teeth on the pivot ratchet. The mechanism also has a pivot thumb piece that is pivotally attached to the pawl key. The thumb piece is used to release the pawl key when it is activated. A rocker thumb piece is mounted on the dual ratchet holder. It is used to engage and disengage a tooth on the stem of a surgical retractor blade.

8 Claims, 3 Drawing Sheets

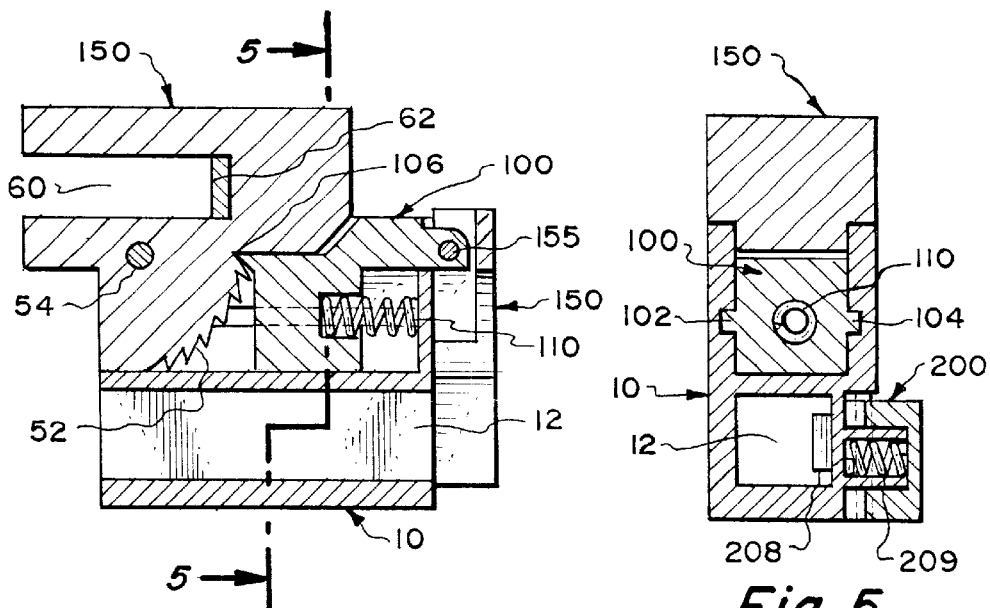
Fig. 4.
Fig. 5.
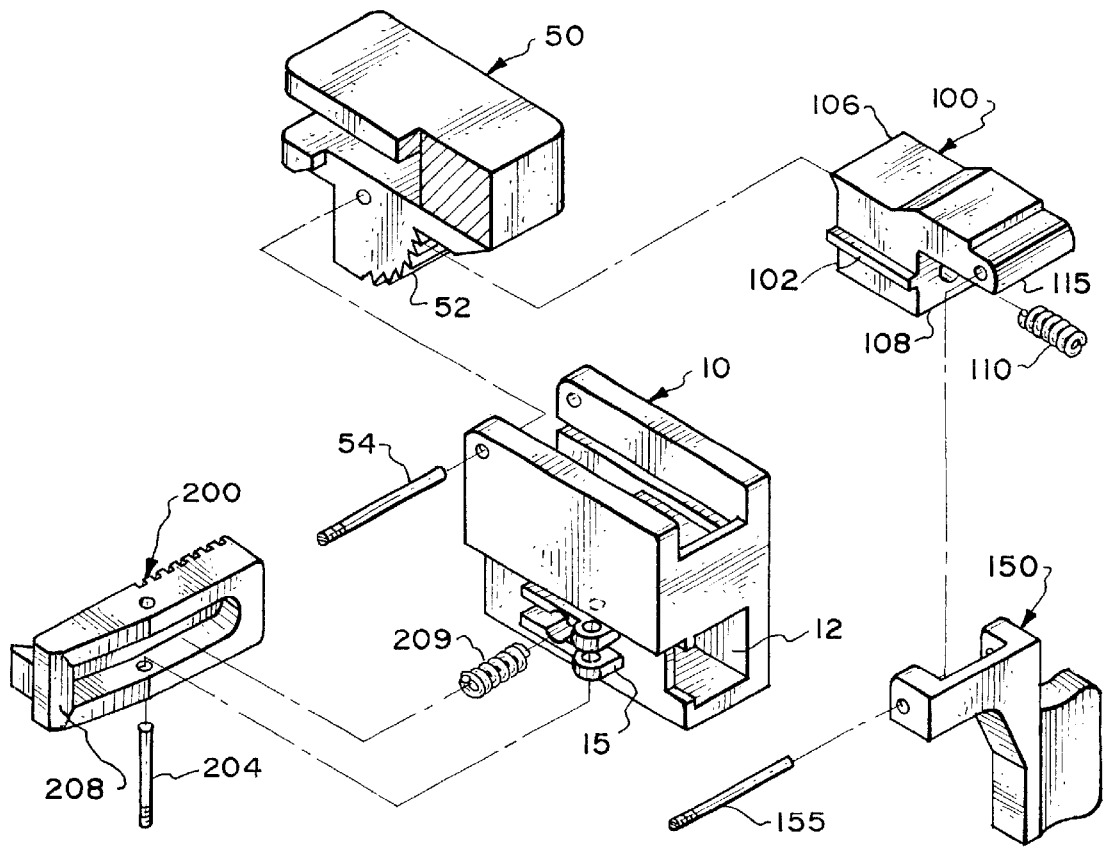
Fig. 6.

RATCHET MECHANISM FOR A SURGICAL RETRACTOR ASSEMBLY

CROSS REFERENCE TO RELATED APPLICATIONS

This is a continuation-in-part of Ser. No. 29/059,029 filed on Aug. 30, 1996 and which will issue on Sep. 1, 1998 as U.S. Design Pat. No. D397791.

BACKGROUND OF THE INVENTION

1. Field of the Invention

The present invention pertains to the following areas of technology:
MACHINE ELEMENTS AND MECHANISMS—intermittent grip type ratchet and pawl.

2. Description of the Prior Art

U.S. Pat. No. 4,424,724 issued on Jan. 10, 1984 to Bookwalter and assigned to Codman & Shurtleff, Inc. discloses a prior art ratchet mechanism for a retractor assembly. FIG. 1 in Bookwalter discloses the surgical environment where the present invention can be utilized. The present invention is an unobvious improvement over the Bookwalter device.

SUMMARY AND OPERATION OF THE INVENTION

The present invention is a ratchet mechanism for a surgical retractor assembly. A surgical retractor assembly is illustrated in FIG. 7. FIGS. 1–6 do show not show the correct orientation of the invention when used with the surgical ring. In FIG. 1, the invention should be rotated 180 degrees about the axis of the blade stem. That would then be the position of the mechanisms illustrated in FIG. 7. It should be emphasized that the present invention can be used wherever any dual ratchet mechanism can be utilized and not just in the environment in FIG. 7.

The present invention secures a retractor blade to a ring placed around and above the surgical sight. The present invention has two ratchet and pawl mechanisms described as a rocker ratchet and a pivot ratchet. The rocker ratchet allows the toothed stem portion of the retractor blade to slide back and forth in the housing or ratchet holder. The surgeon can set the distance and the rocker ratchet and pawl mechanism locks the stem in the ratchet holder. The pivot ratchet and pawl mechanism tilts the stem of the retractor blade relative to the ring. The pivot ratchet mechanism allows the surgeon to tilt downwardly the stem and blade tooth by tooth on the pivot ratchet until the angle of inclination is correct. The angle is automatically locked and the blade cannot be raised unless the pivot thumb piece is released to allow the pawl key to be released to allow the blade to be raised upwardly. The pivot ratchet has a transverse slot that fits over the ring in a radial fashion as illustrated in FIG. 1. The slot abuts against the outer edge of the ring, which has indentations. A dowel pin in the slot engages one of the indentations on the ring to help keep the ratchet mechanism from sliding along the ring. As the surgeon pulls on the end of the blade stem to secure the blade in the incision, the counter force of the slot in the pivot mechanism pressing against the outer edge of the ring keeps the mechanism temporarily but securely in position during the surgery. If it becomes necessary, the surgeon can easily adjust the position of the surgical blade by releasing either the rocker thumb piece and/or the pivot thumb piece to reset the distance and tilt of the blade and can then easily relock the stem to its new position. After the surgery, the pieces are all easily separated and sterilized for reuse.

BRIEF DESCRIPTION OF THE DRAWINGS

FIG. 4 is a sectional view taken along line 4—4 in FIG. 1.

FIG. 5 is a sectional view taken along line 5—5 in FIG. 4.

FIG. 6 is an exploded perspective view of the ratchet mechanism for a surgical retractor assembly.

DETAILED DESCRIPTION OF THE INVENTION

Figure 1:
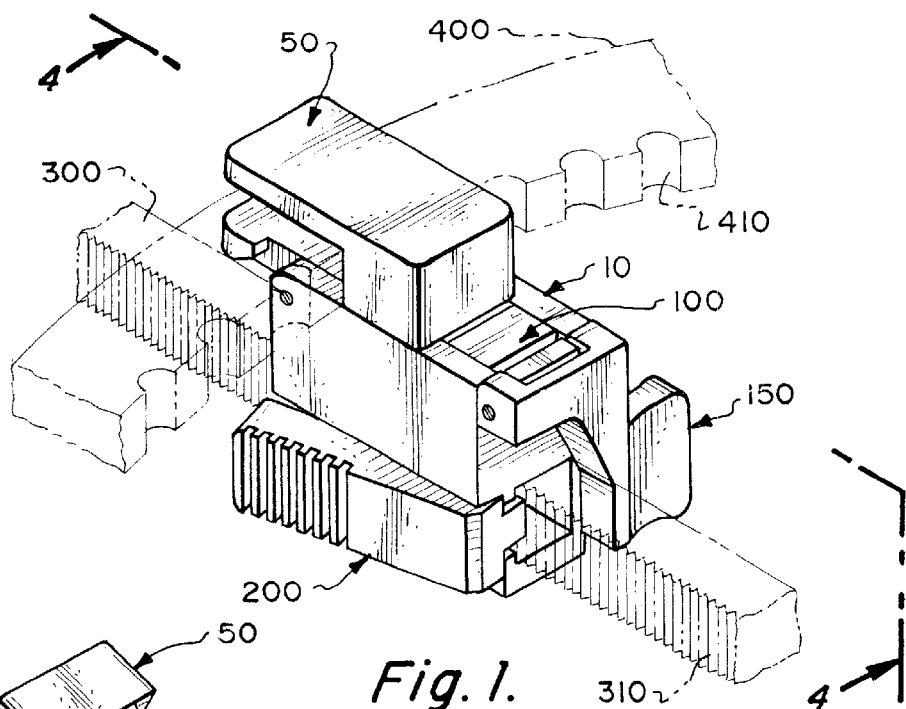
FIG. 1 is a perspective view of a ratchet mechanism for a surgical retractor assembly. The toothed stem portion of a surgical retractor blade with a ratchet on one side is shown in broken lines.

The present invention will now be discussed in detail. FIG. 6 is an exploded perspective view and illustrates the five major components that comprise the invention. The present invention consists of a dual ratchet holder 10, a pivot ratchet 50, a pawl key 100, a pivot thumb piece 150, a rocker thumb piece 200, three pivot pins and two compression springs.

The dual ratchet holder 10 has a surgical blade stem slot 12 running axially through the holder. A section 300 of a type of retractor blade stem is illustrated in broken lines in FIG. 1. The ratchet holder has a cutaway lower shelf with a projection 15 for mounting the rocker thumb piece 200. The rocker thumb piece 200 is mounted to the projection 15 with a pivot pin 204. A compression spring 209 biases the rocker thumb piece to keep the rocker thumb piece in the closed locked position unless the rocker is depressed to release the detent 208 on the rocker. The surgical stem 300 has a series of teeth 310 along one side as illustrated in FIG. 1. The detent 208 mates with any one of the teeth on the stem so that the surgical stem cannot move relative to the present invention while the rocker is not touched. In the preferred embodiment, the detent allows the toothed stem to pass through the housing towards the right in FIG. 1. This shortens the distance of the surgical blade relative to the surgical ring 400. A section of the ring 400 is also illustrated in FIG. 1. The surgeon positions the blade in the incision and then pulls on the end of the stem 300 until the blade holds the organs or other tissues in position for the operation. Actually about six blades are mounted and positioned at about the same time after the incision to keep the ring in the proper position.

Figure 2:
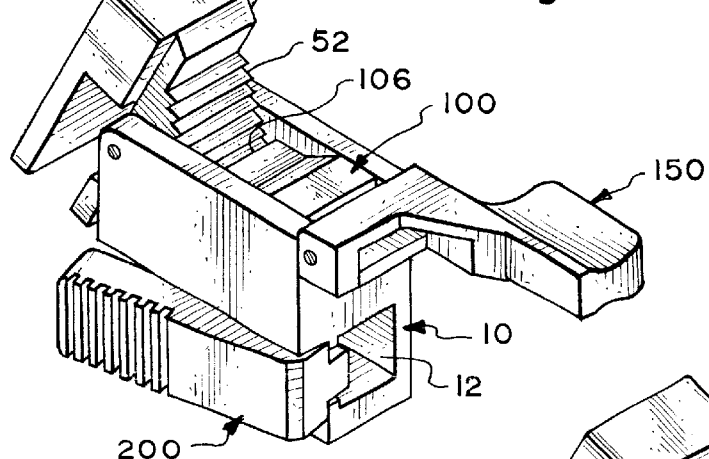
FIG. 2 is a perspective view of the ratchet mechanism for a surgical retractor assembly with the pivot thumb piece and pawl key in the open position.
Figure 3:
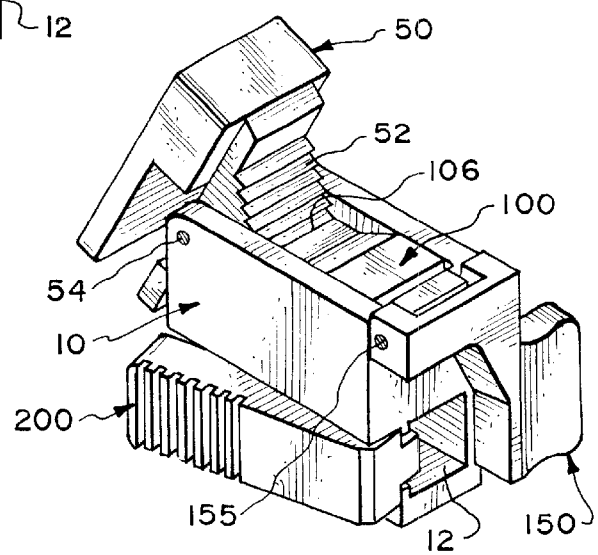
FIG. 3 is a perspective view of the ratchet mechanism for a surgical retractor assembly with the pawl key in the closed position.
Figure 7:
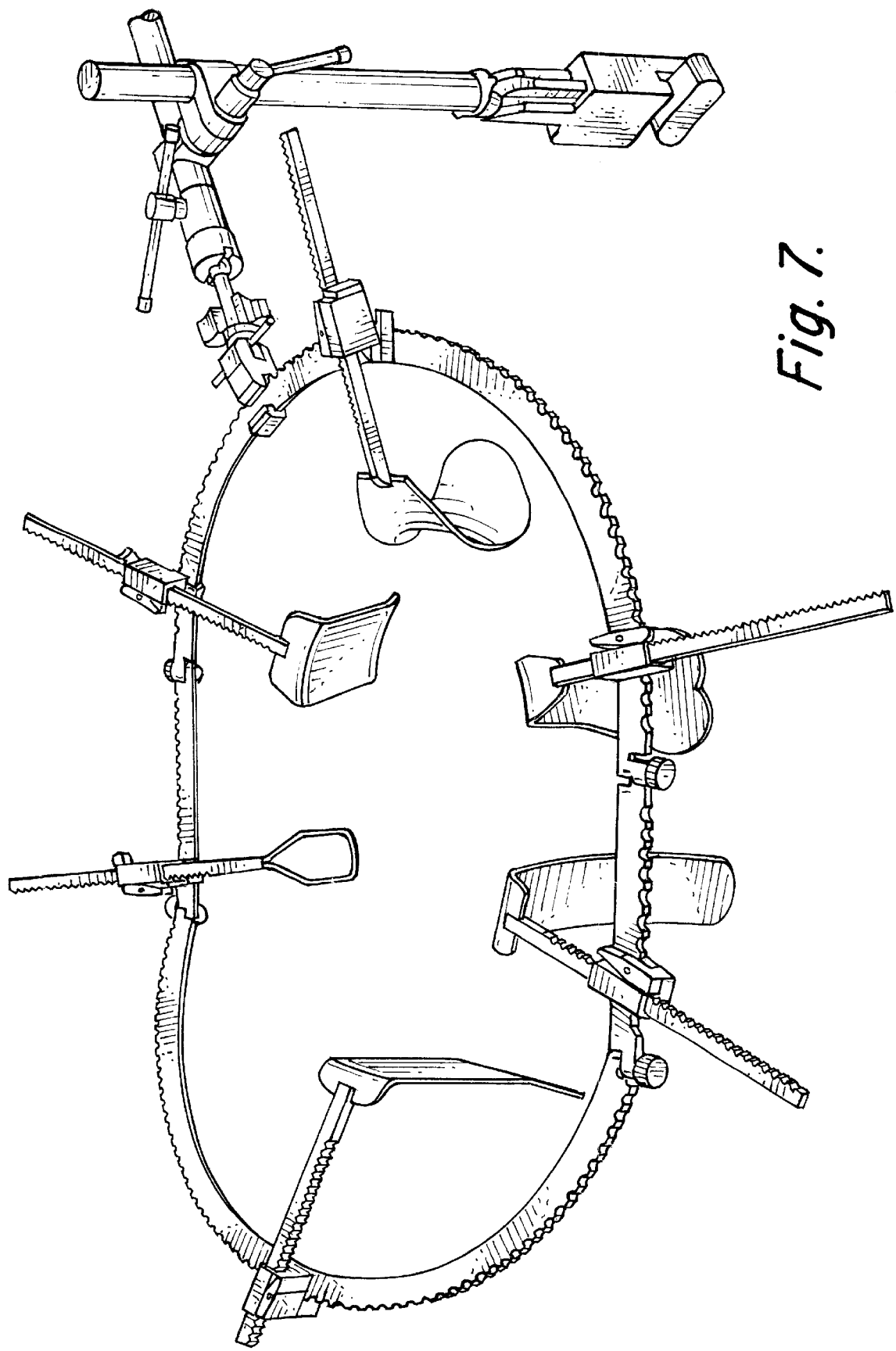
FIG. 7 illustrates a perspective view of a complete surgical retractor assembly and illustrates the present invention used to hold six surgical blades to a segmented surgical ring. This assembly is used during abdominal and other surgical procedures.

The top of the dual ratchet holder has a cavity cut away for mounting the pivot ratchet 50 and the pawl key 100. The pivot ratchet has a series of teeth 52 formed in a semicircular manner. The teeth are inclined as clearly shown in the cross section of FIG. 4. A pivot pin 54 is mounted transversely relative to the pivot ratchet to allow the pivot ratchet to pivot within a range of about 70 degrees relative to the axis of the stem 300. The maximum range position of the pivot ratchet is illustrated in FIGS. 2 and 3.

The cavity in the dual ratchet holder also has a guideway for allowing the pawl key 100 to reciprocate sufficiently to allow the edge 106 to disengage a tooth 52. The guideway is illustrated in the cross section of FIG. 5 and in the perspective view of FIG. 6. The guideway is illustrated as a pair of opposed tongue and groove sliding joints 102 and 104. The pawl key includes a transverse edge 106 that mates with one of the inclined teeth 52 on the pivot pawl. This is a classic ratchet and pawl structure. The edge 106 allows the pawl to pivot counterclockwise in FIG. 4 tooth by tooth when tilting the retractor blade, but the ratchet cannot pivot clockwise unless the pawl key is released. The front of the key has a stop 108 and a compression spring 110 interposed between the stop 108 and the right vertical face of the cavity in the ratchet holder. This prevents the key from sliding out of the tongue and grooves and also biases the key against the ratchet pawl. The thumb release member 150 is mounted to an overhang 115 on the key. A pivot pin 155 secures the thumb release member 150 to the key. FIG. 2 shows the thumb release 150 in the open unlocked position. This allows the ratchet to pivot clockwise to reset the blade stem back to the horizontal position. FIG. 3 shows the thumb piece 150 in the locked position with the ratchet pivoted to its maximum angle. The pivot ratchet has a slot 60. FIG. 1 shows a portion of the ring 400 in the slot. The slot is located transversely relative to the axis of the blade stem. A vertical dowel pin 62 is located in the slot to engage an indentation 410 on the ring. The dowel 7 pin can be seen in the cross section of FIG. 4. The function of the slot is discussed in the summary of the invention.

While the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A ratchet mechanism for a surgical retractor blade comprising:
    a dual ratchet holder;
    a pivot ratchet mounted on said dual ratchet holder;
    a pawl key mounted on said dual ratchet holder for linear movement and engaging said pivot ratchet;
    a pivot thumb piece pivotally attached to said pawl key for releasing said pawl key when activated; and
    a rocker thumb piece mounted on said dual ratchet holder for engaging and disengaging a tooth on a stem.

2. The ratchet mechanism as recited in claim 1 wherein:
    said pivot ratchet is pivotable relative to the axis of the stem; and
    said rocker thumb piece allows said ratchet mechanism to reciprocate relative to the axis of the stem.

3. The ratchet mechanism as recited in claim 1 wherein:
    said pivot ratchet is pivotable relative to the axis of the stem.

4. The ratchet mechanism as recited in claim 1 wherein:
    said rocker thumb piece allows said ratchet mechanism to reciprocate relative to the axis of the stem.

5. The ratchet mechanism as recited in claim 1 wherein:
    said pawl key slides along a tongue and groove channel.

6. The ratchet mechanism as recited in claim 1 wherein:
    said dual ratchet holder has a blade stem slot running axially therethrough.

7. The ratchet mechanism as recited in claim 1 wherein:
    said pivot ratchet has a semicircular array of teeth.

8. The ratchet mechanism as recited in claim 1 wherein:
    said pivot ratchet can pivot within a range of 70 degrees relative to the stem.

* * * * *